United States Patent
Gandy et al.

(10) Patent No.: US 10,860,688 B1
(45) Date of Patent: Dec. 8, 2020

(54) SYSTEM AND METHOD FOR ENCOURAGING A MEDICAL PATIENT TO COMPLETE MEDICAL TREATMENT REGIMEN

(71) Applicant: Play-it Health, Inc., Kansas City, KS (US)

(72) Inventors: Kimberly L. Gandy, Kansas City, KS (US); Erica Domen, Kansas City, KS (US); Virginia Savin, Kansas City, MO (US)

(73) Assignee: Play-it Health, Inc., Overland Park, KS (US)

( * ) Notice: Subject to any disclaimer, the term of this patent is extended or adjusted under 35 U.S.C. 154(b) by 48 days.

(21) Appl. No.: 13/974,562

(22) Filed: Aug. 23, 2013

Related U.S. Application Data

(60) Provisional application No. 61/693,283, filed on Aug. 25, 2012.

(51) Int. Cl.
    *G06F 19/00* (2018.01)
    *G16H 20/00* (2018.01)

(52) U.S. Cl.
    CPC ......... *G06F 19/3456* (2013.01); *G16H 20/00* (2018.01)

(58) Field of Classification Search
    CPC .... G06F 19/3456; G16H 20/10; G16H 20/60; G16H 20/70; G16H 20/90
    USPC ........................................................ 705/2–3
    See application file for complete search history.

(56) References Cited

U.S. PATENT DOCUMENTS

| | | | | |
|---|---|---|---|---|
| 5,966,526 A * | 10/1999 | Yokoi | ................... | A63F 13/005 703/11 |
| 6,102,855 A * | 8/2000 | Kehr | ................... | A61B 5/0002 206/561 |
| 7,104,884 B2 * | 9/2006 | Yokoi | ................... | A63F 13/005 463/7 |
| 8,706,523 B2 * | 4/2014 | Kulawiec et al. | ................ | 705/2 |
| 8,775,196 B2 * | 7/2014 | Simpson | ............. | G06F 19/3418 705/2 |
| 8,982,133 B2 * | 3/2015 | Zajac, III | ................ | A63F 13/10 345/473 |
| 2002/0160835 A1 * | 10/2002 | Fujioka | ................... | A63F 13/10 463/31 |
| 2005/0021372 A1 * | 1/2005 | Mikkelsen | ............... | A61B 5/00 705/2 |

(Continued)

FOREIGN PATENT DOCUMENTS

WO    WO-2013165761 A1 * 11/2013  ............. A63F 13/44

OTHER PUBLICATIONS

Ramsay, "Virtual Pets and Virtual Selves as Exercise Motivation Tools", 2015, MIT (Year: 2015).*

*Primary Examiner* — Elaine Gort
*Assistant Examiner* — Amanda R. Covington
(74) *Attorney, Agent, or Firm* — Erise IP, P.A.

(57) ABSTRACT

Medical patients do not always diligently follow their treatment plans. A medical treatment system that helps medical patients to follow their prescribed medical treatment plans. The medical treatment system includes a medical treatment application program that alerts a patient when a treatment step is required, rewards the patient with a virtual reward if the treatment step is completed, and reminds the patient if a treatment step has not yet been performed.

19 Claims, 5 Drawing Sheets

(56) References Cited

U.S. PATENT DOCUMENTS

| | | | |
|---|---|---|---|
| 2005/0101845 A1* | 5/2005 | Nihtila | A61B 5/0002 600/300 |
| 2006/0139150 A1* | 6/2006 | Brue | A61J 7/0481 340/309.16 |
| 2007/0168228 A1* | 7/2007 | Lawless | 705/2 |
| 2008/0077437 A1* | 3/2008 | Mehta | G06Q 30/02 705/2 |
| 2010/0082367 A1* | 4/2010 | Hains | G06F 19/3456 705/2 |
| 2010/0125182 A1* | 5/2010 | Schroeter | G06F 19/3418 600/301 |
| 2012/0021823 A1* | 1/2012 | Youm | A63F 13/795 463/29 |
| 2012/0117020 A1* | 5/2012 | Davis | G16H 50/20 706/54 |
| 2012/0136218 A1* | 5/2012 | Lee | G06F 19/3418 600/300 |
| 2013/0096953 A1* | 4/2013 | Beverly | G06F 19/3418 705/3 |
| 2013/0138450 A1* | 5/2013 | Vigneux | G06F 19/34 705/2 |
| 2014/0088393 A1* | 3/2014 | Bernstein | G06F 19/3456 600/365 |

* cited by examiner

SYSTEM AND METHOD FOR ENCOURAGING A MEDICAL PATIENT TO COMPLETE MEDICAL TREATMENT REGIMEN

RELATED APPLICATIONS

This application claims priority to U.S. Patent Application Ser. No. 61/693,283, filed Aug. 25, 2012, and entitled "System and Method for Encouraging a Medical Patient to Complete Medical Treatment Regimen," which is incorporated herein by reference in its entirety.

FIELD OF INVENTION

The present invention relates to the field of computer applications. In particular, but not by way of limitation, the present disclosure teaches a system and techniques for helping medical patients to properly complete their prescribed medical treatment regimens.

BACKGROUND

To properly treat a medical condition, medical patients must co-operate with medical professionals in order to complete a medical treatment regimen. The amount of cooperation from medical patients can vary significantly. A cooperative and diligent medical patient can make medical treatment easy. However, an uncooperative and/or forgetful patient can make providing medical treatment very difficult for medical professionals. For example, very young children and elderly patients with memory issues can make it very challenging for a medical professional to provide proper medical treatment if these patients do not diligently take the required medicines and/or perform other tasks needed for a particular medical treatment.

Various infectious diseases often require a type of medical treatment regimen that is very difficult for uncooperative and/or forgetful patients to follow completely. Specifically, the medical treatment for an infectious disease may require consistently and fully consuming a set of medications according to a prescribed protocol. Uncooperative or forgetful patients often fail to completely fulfill the prescribed medical protocol. Many of these patients start off by accurately following the prescribed medical regimen. However, as the symptoms from the infectious disease fade away and the patient begins to feel better, the compliance with the prescribed medical protocol often drops.

Not fully complying with a properly prescribed medical protocol can have significant adverse consequences on the patient. In some cases, the infectious disease may simply become less noticeable but not actually be cured. During this time, the patient may infect other people that the patient comes in contact with. The disease may then re-infect the patient thus requiring the patient to restart the prescribed medical protocol all over again.

Furthermore, not fully complying with a prescribed medical protocol may even cause harm to the greater community. By stopping a prescribed antibiotic protocol prematurely some of the bacteria causing the infection may survive. The surviving bacteria may be the bacteria with the greatest resistance to the prescribed antibiotic. The end result may be that the bacterial population in the afflicted patient having a higher than normal resistance to that antibiotic. As this surviving bacteria reproduces, the resulting infection may no longer be treatable using the same antibiotic. Thus, increasingly dangerous strains of untreatable bacteria pathogens may develop from patients that do not properly complete their prescribed medical regimens. Since there are significant adverse consequences to having patients not fully and accurately complete their prescribed medical protocols it would be very desirable to provide means to improve patient compliance with their prescribed medical protocols.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show illustrations in accordance with example embodiments. These embodiments, which are also referred to herein as "examples," are described in enough detail to enable those skilled in the art to practice the invention. It will be apparent to one skilled in the art that specific details in the example embodiments are not required in order to practice the present invention. For example, although some of the embodiments are disclosed with reference to an application program for use on mobile telephones, the teachings of the present disclosure may be used with many other types of computer systems used by patients such as personal computers, tablet computers, and thin-client devices. The example embodiments may be combined, other embodiments may be utilized, or structural, logical and electrical changes may be made without departing from the scope of what is claimed. The following detailed description is, therefore, not to be taken in a limiting sense, and the scope is defined by the appended claims and their equivalents.

In this document, the terms "a" or "an" are used, as is common in patent documents, to include one or more than one. In this document, the term "or" is used to refer to a nonexclusive or, such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Computer Systems

Figure 1:
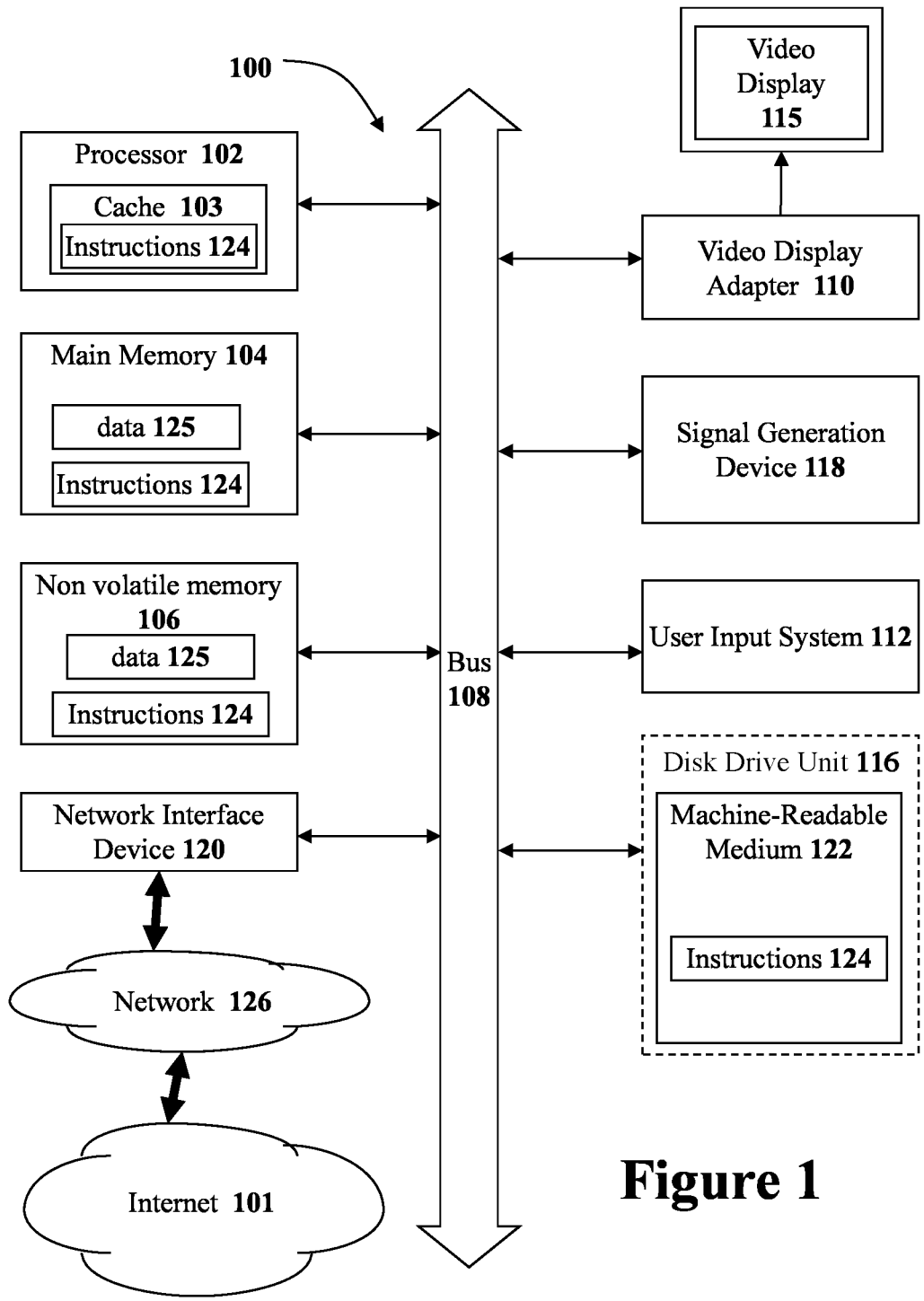
FIG. 1 illustrates a diagrammatic representation of machine in the example form of a computer system within which a set of instructions, for causing the machine to perform any one or more of the methodologies discussed herein, may be executed.

The present disclosure concerns digital computer systems. FIG. 1 illustrates a diagrammatic representation of a machine in the example form of a computer system 100 that may be used to implement portions of the present disclosure.

In a networked deployment, the machine of FIG. 1 may operate in the capacity of a server machine or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, a network switch, a network bridge, a video game console, or any machine capable of executing a set of computer instructions (sequential or otherwise) that specify actions to be taken by that machine. Furthermore, while only a single machine is illustrated, the term "machine" shall also be taken to include any collection of machines that individually or jointly execute a set (or multiple sets) of instructions to perform any one or more of the methodologies discussed herein.

The example computer system 100 of FIG. 1 includes a processor 102 (e.g., a central processing unit (CPU), a graphics processing unit (GPU) or both), a main memory 104, and a non-volatile memory 106, which communicate with each other via a bus 108. The processor 102 is hardware. The non-volatile memory 106 may comprise flash memory and may be used either as computer system memory, as a file storage unit, or both. The main memory 104 and/or the non-volatile memory 106 may store instructions 124 and data 125 that are processed by the processor 102 to perform any one or more of the methodologies (i.e. features) discussed within the present disclosure.

The computer system 100 may include a video display adapter 110 that drives a video display system 115 such as a Liquid Crystal Display (LCD) in order to display visual output to a user. The computer system 100 may also include other output systems such as signal generation device 118 that drives an audio speaker.

Computer system 100 includes a user input system 112 for accepting input from a human user. The user input system 112 may include an alphanumeric input device such as a keyboard, a cursor control device (e.g., a mouse or trackball), a microphone, or any other device for accepting input from a human user. In the case of cellular telephone or a tablet computer system, the user input system 112 may comprise in part a touch sensitive pad that may be overlaid on top of video display 115 and a set of buttons.

The computer system 100 may include a disk drive unit 116 for storing data. The disk drive unit 116 includes a machine-readable medium 122 on which is stored one or more sets of computer instructions and data structures (e.g., instructions 124 also known as 'software') embodying or utilized by any one or more of the methodologies or functions described herein. The instructions 124 may also reside, completely or at least partially, within the main memory 104 and/or within a cache memory 103 associated with the processor 102. The main memory 104 and the non-volatile memory 106 associated with the processor 102 also constitute machine-readable media.

The computer system 100 may include one more network interface devices 120 for transmitting and receiving data on one or more networks 126. For example wired or wireless network interfaces 120 may couple to a local area network 126. Similarly, a cellular telephone network interface 120 may be used to couple to a cellular telephone network 126. The various different networks 126 are often coupled directly or indirectly to the global internet 101. The instructions 124 and data 125 used by computer system 100 may be transmitted or received over network 126 via the network interface device 120. Such transmissions may occur utilizing any one of a number of well-known transfer protocols such as the well-known File Transport Protocol (FTP).

Note that not all of the parts illustrated in FIG. 1 will be present in all embodiments. For example, a computer server system may not have a video display adapter 110 or video display system 115 if that server is controlled through the network interface device 120. Similarly, a tablet computer or cellular telephone will generally not have a disk drive unit 116.

While the machine-readable medium 122 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies described herein, or that is capable of storing, encoding or carrying data structures utilized by or associated with such a set of instructions. The term "machine-readable medium" shall accordingly be taken to include, but not be limited to, solid-state memories, optical media, battery-backed RAM, and magnetic media.

For the purposes of this specification, the term "module" includes an identifiable portion of code, computational or executable instructions, data, or computational object to achieve a particular function, operation, processing, or procedure. A module need not be implemented in software; a module may be implemented in software, hardware/circuitry, or a combination of software and hardware.

Medical Treatment Regimens

Various medical conditions often require a medical treatment regimen that must be rigorously followed in order to cure the patient. For example, an infection may require that a patient diligently take a set of antibiotics or a physical injury may require a patient to follow a set of specified physical therapy exercises.

Some patients may be uncooperative, forgetful, or too lazy such that some patients will fail to follow the prescribed medical treatment regimen. For example, a prescribed medical treatment may require that a patient consistently and fully consume a set of medications according to a prescribed protocol but that patient may fail to completely fulfill the prescribed medical protocol. With an anti-biotic medical regimen many patients start off by accurately following the prescribed medicine protocol. However, as the patient's symptoms from the infection fade away and the patient begins to feel better, the patient may stop taking the required medication. Once the patient's symptoms subside, the patient may lose the incentive to take the medication. Thus medical patients frequent discontinue prescribed medical treatment regimens prematurely.

Prematurely discontinuing a prescribed medical treatment can have several different adverse consequences. One obvious consequence is that the illness being treated may reappear in the patient since it was never fully cured. With infectious diseases, this also puts other people at risk since the people around the patient may become infected. Failing to fully cure a bacterial infection can also contribute to the creation of anti-biotic resistant strains of the disease. Thus, it would be desirable to provide means for encouraging and ensuring that patients fully follow their prescribed medical treatment regimens.

Medical Treatment Application Program Overview

To encourage and ensure that medical patients fully follow their prescribed medical treatment regimens the present application introduces a medical treatment application program. The medical treatment application program is designed to remind the patient when medicine must be taken or other medical treatments must be performed. Furthermore, the medical treatment application program also provides encouragement through a rewards system.

In one embodiment the system of the present application uses an avatar or other representation in a computer application to reward the patient for properly following their medical regimen. For example, an avatar of a sick animal may be presented to the medical patient. As the patient diligently proceeds through his medical regimen, the sick animal slowly begins to recover from its illness. If the patient fails to follow the prescribed medical treatment regimen, the sick animal avatar will not recover and the patient will be reminded to follow the prescribed medical treatment regimen. If the patient continues to fail to follow the prescribed medical treatment regimen then related caregivers and the doctor's office may be notified by the application.

The use of a sick avatar (or other representation) helps emphasize the importance of continuing to follow the prescribed medical treatment regimen even when the patient may lose interest. Specifically, even though the symptoms in the real patient will begin to fade away after taking part of a medicine program, the sick animal avatar will remain visually sick until the patient completes the entire prescribed medical regimen. In this manner, even though the patient's own symptoms may be gone the medical treatment application program is able to use the patient's empathy for the sick animal avatar as motivation to keep taking the medication until the sick animal is fully cured.

Medical Treatment Application Program

The medical treatment application program may be implemented in a variety of different manners. The goal of the various implementations is to remind the medical patient to follow the prescribed medical regimen and to reward the medical patient when the medical patient faithfully follows the prescribed medical regimen.

In one embodiment, a puzzle game approach is used. With the puzzle game approach, the medical treatment application program will show a virtual puzzle piece each time the patient follows a particular medical treatment step from the prescribed medical regimen. For example, the patent may be given a virtual puzzle piece when a patient with a bacterial infection takes a pill from his antibiotic regimen. The puzzle game may start out with a picture of some kind and then fade out leaving only faded puzzle pieces that made up the picture at one point. Then, as the patient takes each pill, a puzzle piece will be provided to the patient.

Upon receiving a puzzle piece, the patient may then drag the puzzle piece to the matching area on the puzzle board. In one embodiment, the puzzle piece will jump up and down and glow until the user drags it to the correct spot. Once the patient drags the puzzle piece to the correct location then the puzzle board may shake and the piece will light up and cover the whole screen in an explosion of light. Depending on the medical regimen the patient is on, the puzzle must be split into the proper number of pieces, but in a random manner. The particular puzzle image may be selected based on the patient such that the patient has an appropriate interesting image.

Note that that medical treatment application program will not allow puzzle pieces to be available until the proper time for the next medical treatment step. The medical treatment application program may show a count-down timer that counts down until the next medical treatment is required.

In another embodiment, the system uses an avatar that that starts in a sick or broken state and must be put back into a well or repaired state. For example, an animal avatar may be used such that the patient will take care of a sick animal by following the same medical treatment regimen schedule for the animal. For example, if the patient is on an antibiotics regimen then each time the patient takes a pill (and informs the medical treatment application program) then the medical treatment application program will also provide a pill to the sick animal avatar. As the medical treatment progresses the animal avatar goes from a sick animal to a healthy animal. In one embodiment, once the patient has progressed through more than one treatment stage, the patient may go back and forth and replay the progression of the sick animal avatar so far.

Note that a sick animal avatar is just one possible avatar that may be used and will be used as the main example in this document. However many other types of avatar progressions may be used: a broken car may progress to a fixed car, a transforming robot may transform from one shape to another shape, a sports team may start with no players and end with a full team, etc. Any set of progressive images may be used.

In one embodiment, both the puzzle game and the avatar game are made available to the user such that the user can select either game. In another embodiment, the patient is allowed to play both games with the regimen the patient is on.

Application Program Distribution

The medical treatment application program may run on various different platforms and may be distributed in various different manners. However, a key application format is for mobile devices such as cellular telephones such that the patient may always carry the medical treatment application program around with them and receive alarms indicating when a medical treatment step is required.

Figure 2:
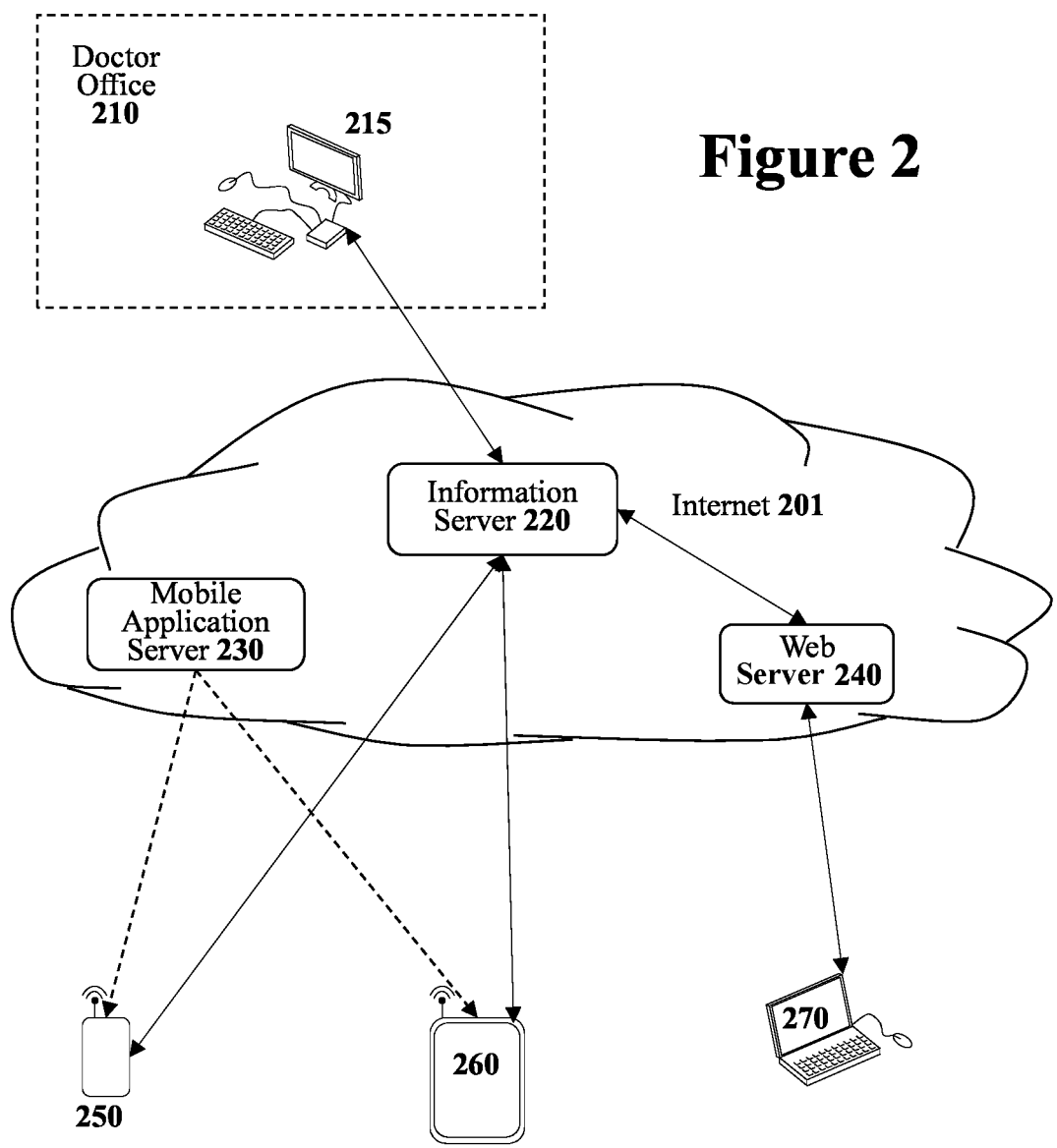
FIG. 2 conceptually illustrates methods that may be used to acquire a medical treatment application program and information needed for a specific patient.

FIG. 2 conceptually illustrates a few different manners in which the medical treatment application program and related information may be distributed. In the simplest form, the medical treatment application program may be made available as a mobile application program on a mobile application server 230 on the internet. For example, the medical treatment application program may be made available on the Apple AppStore, the Android Play Store, the Amazon Appstore for Android, and other similar mobile application distribution platforms.

In another embodiment, the prescribing doctor (or doctor's office) can play a role in the medical treatment application program distribution. When a patent is prescribed a medical treatment program at a doctor's office 210, a person at the doctor's office 210 may use a computer 215 to contact an information server 220 on the internet 201. The person at the doctor's office 210 may first create an account for the doctor if no account has yet been created. Creating an account may involve providing information about the doctor's office such as contact information. In one embodiment, direct patient information is not entered into the information server 220 such that the privacy of the patient is protected.

The person at the doctor's office 210 then enters information about the patient and the prescribed medical treatment program for the patient. For example, with a drug treatment plan the person may enter the drug being prescribed, the schedule for taking the medication, and how many pills must be taken at each time. The person at the doctor's office 210 may also enter contact information about care-givers associated with the patient such as parents, a spouse, or other person that may help with the treatment. After entering the information for the patient, the person at the doctor's office 210 may receive a code that may be used to access the pertinent information. The code may be given to the patient on paper, in an email, texted to the patient's cellphone 250, or otherwise provided to the patient.

The patient may then download the medical treatment application program from a mobile application server 230. Upon activating the medical treatment application program, the medical treatment application program may request the code such that the medical treatment application program can fetch the information about the patient's medical treatment regimen from the information server 220. In one embodiment, clicking on the code texted to the patient's cellphone 250 may cause the patient's cellphone 250 to automatically download the medical treatment application program and the appropriate information for that patient's medical treatment regimen.

After a doctor's office has entered information into the information server 220, the information server 220 may set a watchdog timer to ensure that the patient downloads and begins using the medical treatment application program. If the patient fails to download and use the medical treatment application program within a certain time limit, the information server 220 may notify the doctor's office 210 that a particular patient has not downloaded the program and begun the medical treatment regimen.

Although the cellphone version will be focused upon in this document, other platforms may also be used to implement a medical treatment application program. In one embodiment, a tablet computer system 260 is used in a similar fashion to a cellphone embodiment. In another embodiment, a web-server based version is implemented with a web server 240. By using a web-server based implementation, any platform with a web browser coupled to the internet 201 may be used to access the medical treatment application program. For example a microbrowser on cellphone 250, a web browser on tablet computer 260, a web browser on a personal computer system 270, or any other web browser may access the medical treatment application program version implemented on web server 240. This allows for broad platform support. Note that the web server 240 may receive information from the information server 220.

Medical Treatment Application Program Operation

Figure 3:
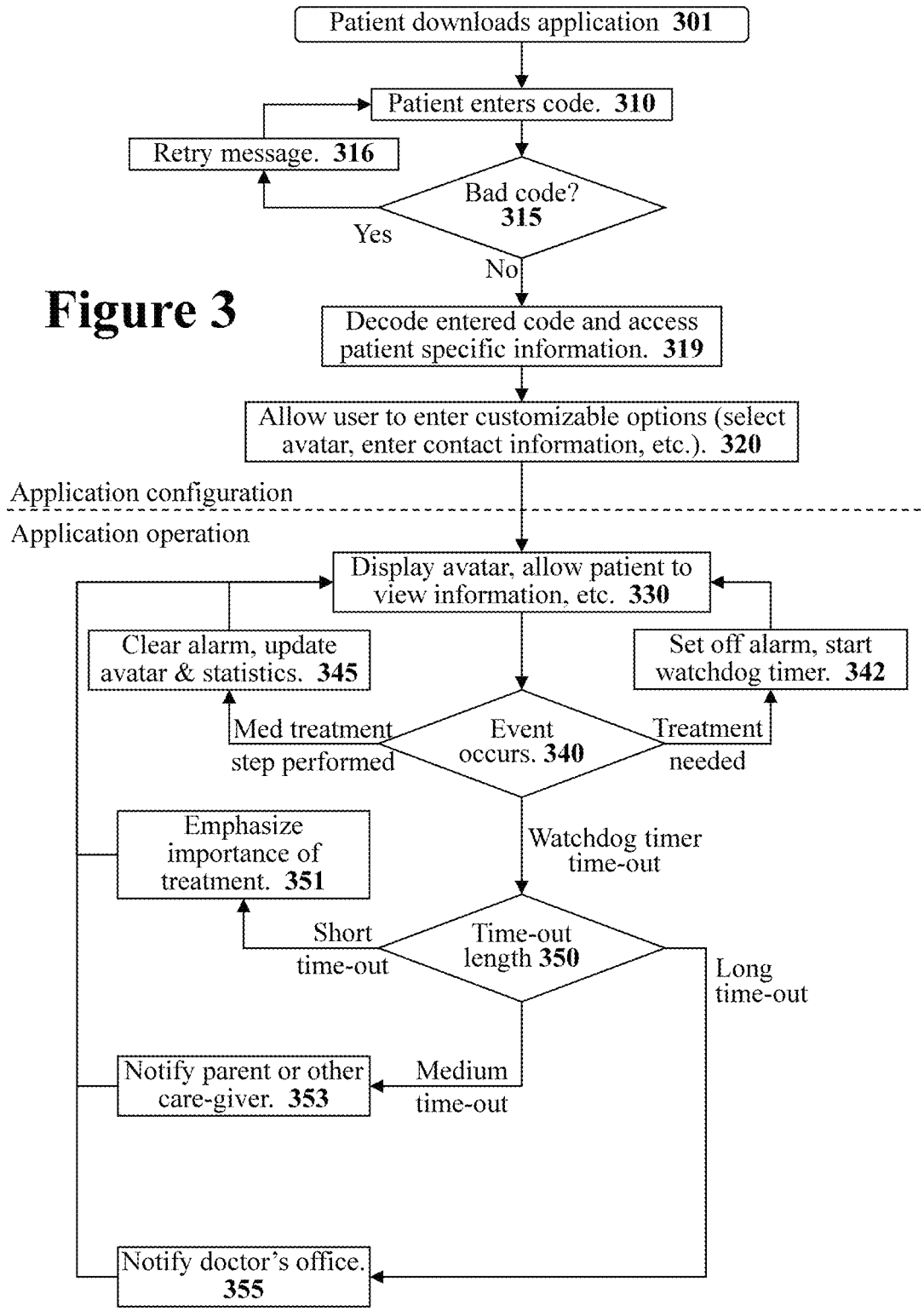
FIG. 3 illustrates a flow diagram that discloses the operation of a medical treatment application program for encouraging patients to follow their medical treatment regimen.

To fully disclose the medical treatment application program, this section describes the operation of a medical treatment application program. FIG. 3 illustrates a flow diagram that discloses the operation of various different embodiments of a medical treatment application program.

Initially, at stage 301, the patient downloads the medical treatment application program. As set forth earlier, the medical treatment application program may be obtained from a web site, a mobile application store, or other suitable server.

The next few steps configure the medical treatment application program. Depending on the particular embodiment, certain steps may be omitted. For example, in an embodiment that automatically receives the needed patient information; the system can skip down to step 319.

In a system wherein the patient is given a code from the doctor's office, the patient enters the code at stage 310. The system tests the entered code at stage 315. If a bad code has been entered, the patient is given a message at stage 316 suggesting that the patient re-enter the code or contact the doctor's office for a new code if the code continues not to work.

When a proper code has been entered the system proceeds to stage 319 where the entered code is decoded. In one embodiment, the code itself contains the information required for the patient's medical regimen such as how often medicine must be taken, when it should be taken, and how much to take. In another embodiment, the code directs the medical treatment application program to access the information server 220 to obtain additional information about this specific patient. As set forth earlier, the information obtained from the information server 220 may include information about the specific medical regimen, contact information for care-givers related to the patient, contact information related to the doctor's office, links to additional information about the patient's medical condition, etc.

The medical treatment application program then proceeds to stage 320 where the user is able to enter customizable option information. The user may enter contact information for the doctor's office and/or an associated care-giver such as a parent or spouse at this point.

Figure 5:
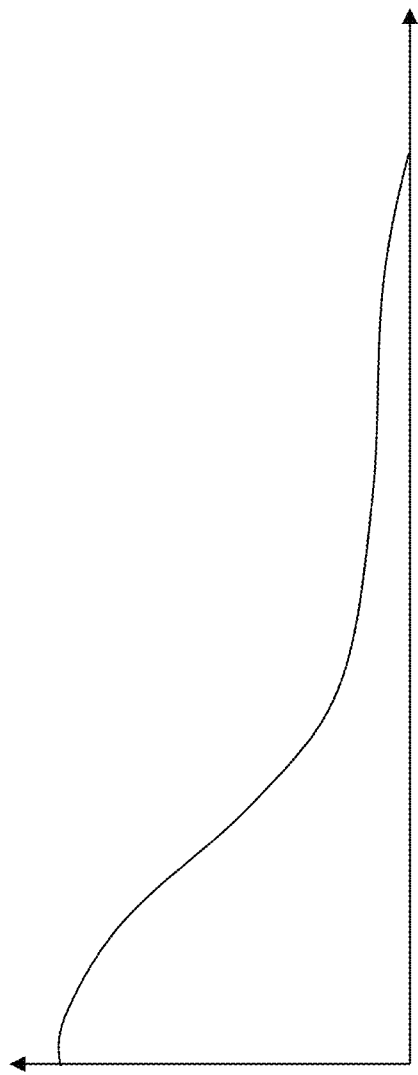
FIG. 5 illustrates a graph showing an example bacterial infestation level in a patient over a period of time when a prescription antibiotic is administered properly at prescribed intervals.

FIG. 5 illustrates a graph showing an example bacterial infestation level in a patient over a period of time when a prescription antibiotic is administered properly at prescribed intervals. In some embodiments that do not use a patient code, the patient may need to select a specific medical treatment protocol at this stage such as a typical 7, 10, or 14 day medicine protocol with medicine taken once, twice, or four times a day. Typical time courses for antibiotics are 7, 10, and 14 day courses. Typical dosages are two times a day to 4 times a day. The following patterns may be used:

7, 14, 21, 28
10, 20, 30, 40
14, 28, 42, 56

This allows for 7, 10 and 14 day courses of meds from twice a day to four times a day.

In an embodiment wherein the patient enters the treatment protocol, the medical treatment application program may send a message to the doctor's office (using the doctor's contact information just entered) informing the doctor's office of the medical regimen entered such that the doctor's office may verify that the proper medical regimen was entered.

Referring again to FIG. 3, at stage 320, the user may select what particular game (such as the puzzle game or avatar game) the user wishes to use. Specific information within the particular game selected such as an animal avatar may be selected. In one embodiment, the medical treatment application program accesses information server 220 to obtain a list of different avatars that may be selected. In this manner, the medical treatment application program can be continually updated with new avatars, puzzles, images, and other media simply by putting new media onto the information server 220. Once selections are made, the medical treatment application program downloads the needed media assets (images, videos, audio files, etc.) from the information server 220.

After completing all the configuration stages, the medical treatment application program begins normal operation at stage 330. In the normal operation stage, the patient can view the current progress of the medical treatment and the associated puzzle/avatar game. The patient may also see a countdown timer indicating when the next medical treatment is required. In some embodiments, the medical treatment application program provides links that allow the patient to learn more about the medical issue that the patient is being treated for. In some embodiments, the patient may be able to switch to a different avatar if desired. The medical treatment application program will remain in the normal operation stage 330 until an event occurs at stage 340.

One event that may occur is that the medical treatment schedule may indicate that a medical treatment step is required for the patient. When a medical treatment step is required the medical treatment application program proceeds to stage 342 where the medical treatment application program sets off some type of alarm to inform the patient that a medical treatment step is required. Depending on the specific platform, the medical treatment application program may emit an alarm sound, vibrate, or otherwise attempt to obtain the attention of the patient to inform the patient that treatment is required.

In addition to setting off an alarm when treatment is required, the medical treatment application program will start a watchdog timer. The watchdog timer will not be stopped until the user has completed the medical treatment step. The watchdog timer is used to progressively escalate the situation if the patient is not following the medical treatment regimen as will be set forth below. After setting off the alarm and setting a watchdog timer, the medical treatment application program will return to stage 330. However, stage 330 will be different since a visual cue that an alarm has gone off will be displayed to inform the user that a medical treatment step is required. In an embodiment with an animal avatar, the sick animal may whimper or cry to indicate that the animal avatar needs attention from the patient.

Returning to stage 340, another event that may occur is that a patient may indicate that a medical treatment step has been performed (the patient has taken their medicine, performed needed physical therapy, or performed any other needed medical treatment step). When the user has performed a needed medical treatment step, the medical treatment application program proceeds to stage 345 where the medical treatment application program clears the alarm, stops the watchdog timer, and updates statistics. In some embodiments, certain statistics may be sent back to the information server 220 such that the doctor's office 210 may monitor compliance. Furthermore, the medical treatment application program rewards the medical patient with a virtual reward.

Figure 4A:
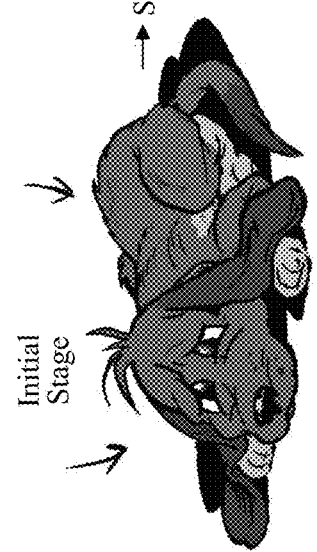
FIG. 4A illustrates a puppy avatar that starts sick and then progresses through a series of intermediate stages until a final stage with a happy healthy puppy.
Figure 4A:
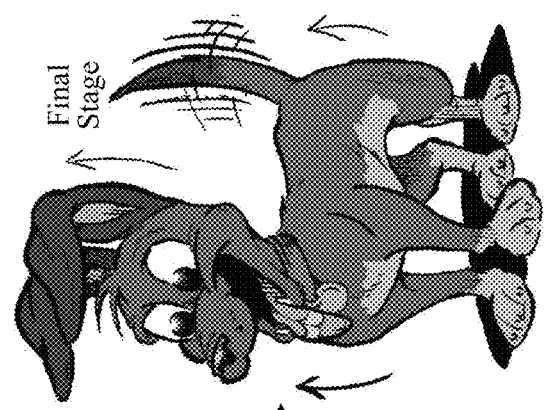
Figure 4B:
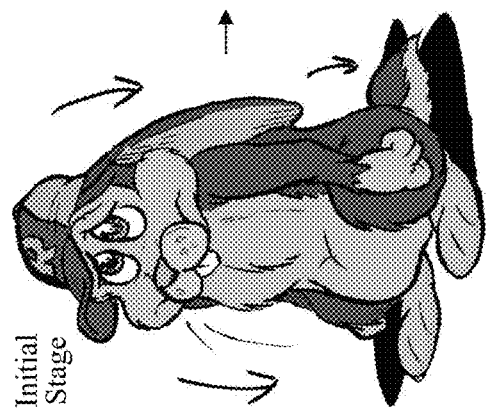
FIG. 4B illustrates a bunny avatar that starts sick and then progresses through a series of intermediate stages until a final stage with a happy healthy bunny.
Figure 4B:
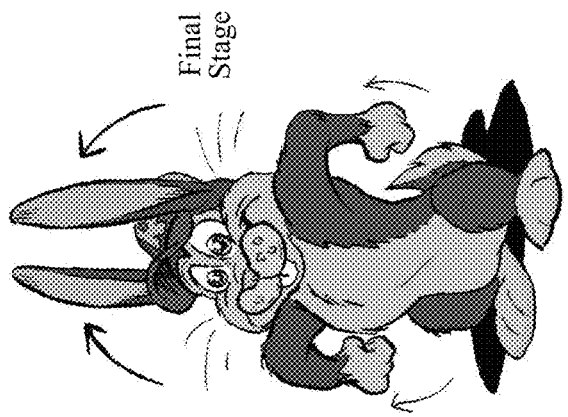

In the case of the avatar game when a sick animal has been selected, the medical treatment application program will update the status display to the next stage of the animal's progression. FIGS. 4A and 4B illustrate two different examples of the first and last avatar of a sick animal. FIG. 4A illustrates a sick puppy that starts very tired and sick and then progresses through a series of intermediate stages until a final stage with a happy alert healthy puppy is displayed. FIG. 4B illustrates a sad weak bunny that will proceed through a set of intermediate stages until a healthy strong bunny is achieved in a final stage.

Returning again to stage 340, if an alarm is active but the patient has not performed the medical treatment step, the watchdog timer started at stage 342 may begin to hit time-out thresholds at stage 350. When a short term time-out is reached, the medical treatment application program proceeds to stage 351 where the alarm to the patient is escalated. A different or louder sound may be emitted. When an animal avatar is being used, the animal avatar may emit more desperate sounds and the treatment progress of the animal avatar may revert to an earlier stage in attempts to get the patient's empathy. The importance of the treatment may be emphasized to the patient by informing the possible adverse consequences of missing treatment steps. The system will then return to stage 330, however the visual display may be changed to emphasize the escalating importance.

Note that only one short-term watchdog timer time-out is illustrated in FIG. 3. However, there may be a series of escalating time-outs that indicate more and more urgency. With the puppy avatar of FIG. 4A, the puppy may whimper like he doesn't feel well if he does not get his med at the first alarm. He may whimper and moan after a second time-out. He may bark if he does not get his medication by the third time-out.

If longer, medium term time-out is encountered at stage 350 then the medical treatment application program may proceed to stage 353 where the medical treatment application program contacts an associated care-giver for the patient such as a parent or spouse. The medical treatment application program may send an email message, a text message, a voicemail, or other type of electronic message to the care-giver informing that care-giver that the patient is not following the prescribed medical treatment protocol. The care-giver may wish to call or otherwise contact the patient and help assist the patent with their medical treatment regimen.

Finally, if an even longer time-out occurs at stage 350 then the medical treatment application program may proceed to stage 355 where the medical treatment application program contacts the doctor's office 210 that prescribed the medical treatment plan. The doctor's office may respond in a variety of ways. The doctor's office may call the patient or an associated care-giver for the patient. The doctor may change the information stored on the information server 220 to change the medical treatment regimen or to display a message on the medical treatment application program.

Upon completing an entire medical treatment regimen, the patient may receive a final virtual reward. The reward may consist of a video, animation, music, or other visual or auditory reward celebration for the patient.

Chronic Medical Treatment Application Program Options

Certain medical conditions require chronic medical treatment such that the patient must continually take medicine. Various different schemes may be used for chronic medicine patients. In one embodiment, an Olympic athlete is used as an avatar. After the patient has taken a certain high number of meds with excellent timeliness, the patient may approach an Olympic Gold.

As the patient's timeliness improves and the athlete moves along the course, the athlete's times also get better. In one embodiment the patient follows the path of an Olympic swimmer that must swim thousands of laps to reach gold. If the patient misses meds, then their avatar's times slow or the avatar may become injured. However, by following the medical treatment plan accurately, the athlete avatar can recover.

When many meds are missed, there is a message to immediately call their coach. The medical treatment application program may also send a message to an associate care-giver or the doctor's office. When associated with specific medical conditions, visual images indicating possible adverse consequences may be displayed. For example, when working on renal transplant issues, the organ may get black spots or shrivel when the patient is not properly taking meds.

The preceding technical disclosure is intended to be illustrative, and not restrictive. For example, the above-described embodiments (or one or more aspects thereof) may be used in combination with each other. Other embodiments will be apparent to those of skill in the art upon reviewing the above description. The scope of the claims should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim is still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. § 1.72(b), which requires that it allow the reader to quickly ascertain the nature of the technical disclosure. The abstract is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A non-transitory computer readable medium having a computer program stored thereon, wherein upon execution the computer program instructs at least one processing element to perform steps comprising:
   downloading medical treatment regimen information to a patient computing device of the patient, wherein the medical treatment regimen information comprises reminders for performing a plurality of steps of a medical treatment regimen;
   monitoring compliance of the patient in performing said plurality of steps;
   presenting, to the patient on the patient computing device, a visual image of a non-human animal avatar,
   wherein the non-human animal avatar has a plurality of stages including a visual health characteristic comprising: an initial stage displaying a visually sick and sad animal, at least one intermediate stage displaying a visually sick and less sad animal having a progressively improved visual appearance, and a final stage displaying a visually healthy and happy animal;
   presenting, to the patient on the patient computing device, a countdown timer indicative of when a next step of the medical treatment regimen is to be performed;
   emitting a first audible cue that is indicative of a first threshold of the countdown timer associated with said next step of the medical treatment regimen,
   emitting a second audible cue that is indicative of a second threshold of the countdown timer associated with said next step of the medical treatment regimen,
   wherein the first audible cue and the second audible cue are non-human animal sounds indicative of the non-human animal avatar, and
   wherein the second audible cue is indicative of an increased urgency relative to the first audible cue, wherein the increased urgency comprises a different type of non-human animal sound and an increased volume to encourage the patient to perform the next step of the medical treatment regimen;
   altering the visual health characteristic of the non-human animal avatar based on said patient's compliance,
   wherein the altering of the visual health characteristic of the non-human animal avatar encourages the patient to improve their compliance with the medical treatment regimen so as to improve the visual health characteristic of the non-human animal avatar,
   wherein compliance by the patient at each step changes the stage of the non-human animal avatar to be closer to the final stage, wherein the non-human animal avatar remains visually sick and sad in all intermediate stages until the patient completes the entire medical treatment regimen.

2. The non-transitory computer readable medium of claim 1, further comprising:
   reminding the patient of each step of the medical treatment regimen; and
   displaying reward information on a display of the patient computing device.

3. The non-transitory computer readable medium of claim 1, further comprising:
   sending a first notification message to a computing device of a lay-person care-giver associated with the patient when the first threshold is crossed; and
   sending a second notification message to a computing device of a medical professional associated with the patient when the second threshold is crossed,
   wherein the second notification message is sent to the medical professional because of an increased severity level.

4. A computerized method comprising:
   downloading medical treatment regimen information to a patient computing device of the patient,
   wherein the medical treatment regimen information comprises reminders for performing a plurality of steps of a medical treatment regimen;
   monitoring compliance of the patient in performing said plurality of steps;
   presenting, to the patient on the patient computing device, a visual image of a non-human animal avatar,
   wherein the non-human animal avatar has a plurality of stages including a visual health characteristic comprising: an initial stage displaying a visually sick and sad animal, at least one intermediate stage displaying a visually sick and less sad animal having a progressively improved visual appearance, and a final stage displaying a visually healthy and healthy animal;
   presenting, to the patient on the patient computing device, a countdown timer indicative of when a next step of the medical treatment regimen is to be performed;

emitting a first audible cue that is indicative of a first threshold of the countdown timer associated with said next step of the medical treatment regimen, emitting a second audible cue that is indicative of a second threshold of the countdown timer associated with said next step of the medical treatment regimen, wherein the first audible cue and the second audible cue are non-human animal sounds indicative of the non-human animal avatar, and wherein the second audible cue is indicative of an increased urgency relative to the first audible cue, wherein the increased urgency comprises a different type of non-human animal sound and an increased volume to encourage the patient to perform the next step of the medical treatment regimen;

altering the visual health characteristic of the non-human animal avatar based on said patient's compliance, wherein the altering of the visual health characteristic of the non-human animal avatar encourages the patient to improve their compliance with the medical treatment regimen so as to improve the visual health characteristic of the non-human animal avatar, wherein compliance by the patient at each step changes the stage of the non-human animal avatar to be closer to the final stage, wherein the non-human animal avatar remains visually sick and sad in all intermediate stages until the patient completes the entire medical treatment regimen.

5. The computerized method of claim 4, further comprising:

reminding the patient of each step of the medical treatment regimen; and displaying reward information on a display of the patient computing device.

6. The computerized method of claim 4, further comprising:

sending a first notification message to a computing device of a lay-person care-giver associated with the patient when the first threshold is crossed; and sending a second notification message to a computing device of a medical professional associated with the patient when the second threshold is crossed, wherein the second notification message is sent to the medical professional because of an increased severity level.

7. The computerized method of claim 4, further comprising:

obtaining additional information about a medical condition of the patient according to input received from the patient.

8. A computerized method comprising:

retrieving, from a server, a set of medical treatment regimen information;

presenting, to a user, a reminder of each step of a medical treatment regimen using the medical treatment regimen information downloaded from the server;

presenting, to the user, a visual image of a non-human animal avatar on a patient computing device, wherein the non-human animal avatar has a plurality of stages including a visual health characteristic comprising: an initial stage displaying a visually sick and sad animal, at least one intermediate stage displaying a visually sick and less sad animal having a progressively improved visual appearance, and a final stage displaying a visually healthy and happy animal;

presenting, to the patient on the patient computing device, a countdown timer indicative of when a next step of the medical treatment regimen is to be performed; and emitting a first audible cue that is indicative of a first threshold of the countdown timer associated with said next step of the medical treatment regimen, emitting a second audible cue that is indicative of a second threshold of the countdown timer associated with said next step of the medical treatment regimen;

wherein the first audible cue and the second audible cue are non-human animal sounds indicative of the non-human animal avatar, wherein the second audible cue is indicative of an increased urgency relative to the first audible cue, wherein the increased urgency comprises a different type of non-human animal sound and an increased volume to encourage the patient to perform the next step of the medical treatment regimen, altering the visual health characteristic of the non-human animal avatar based on said patient's compliance, wherein the altering of the visual health characteristic of the non-human animal avatar encourages the patient to improve their compliance with the medical treatment regimen so as to improve the visual health characteristic of the non-human animal avatar.

9. The computerized method of claim 8, further comprising:

receiving the medical treatment regimen information manually from a user input device of the patient computing device.

10. The non-transitory computer readable medium of claim 1, further comprising treating the sick animal avatar according to the same medical treatment regimen as the patient.

11. The non-transitory computer readable medium of claim 1, further comprising allowing the patient to replay the progression of the sick animal avatar once the patient has progressed through more than one step of the treatment regimen.

12. The non-transitory computer readable medium of claim 1, further comprising presenting, to the patient on the patient computing device, a warning informing the patient of possible consequences of missing the medical treatment.

13. The computerized method of claim 4, further comprising treating the sick animal avatar according to the same medical treatment regimen as the patient.

14. The computerized method of claim 4, further comprising allowing the patient to replay the progression of the sick animal avatar once the patient has progressed through more than one step of the treatment regimen.

15. The computerized method of claim 4, further comprising presenting, to the patient on the patient computing device, a warning informing the patient of possible consequences of missing the medical treatment.

16. The computerized method of claim 8, wherein compliance by the patient at each step changes the stage of the non-human animal avatar to be closer to the final stage, wherein the non-human animal avatar remains visually sick and sad in all intermediate stages until the patient completes the entire medical treatment regimen.

17. The computerized method of claim 8, further comprising treating the sick animal avatar according to the same medical treatment regimen as the patient.

18. The non-transitory computer readable medium of claim 1, wherein the non-human animal sounds are chosen from the group consisting of a whimper, a moan, and a bark.

19. The computerized method of claim 4, wherein the non-human animal sounds are chosen from the group consisting of a whimper, a moan, and a bark.

* * * * *